(12) United States Patent
Courtney, Jr. et al.

(10) Patent No.: US 9,289,218 B2
(45) Date of Patent: Mar. 22, 2016

(54) OSTEOTOME EXTRACTOR

(75) Inventors: Robert Courtney, Jr., Pierceton, IN (US); Jeffrey M. Ondrla, Warsaw, IN (US)

(73) Assignee: Tornier, Inc., Bloomington, MN (US)

( * ) Notice: Subject to any disclaimer, the term of this patent is extended or adjusted under 35 U.S.C. 154(b) by 34 days.

(21) Appl. No.: 13/553,610

(22) Filed: Jul. 19, 2012

(65) Prior Publication Data

US 2013/0261630 A1    Oct. 3, 2013

Related U.S. Application Data

(60) Provisional application No. 61/509,506, filed on Jul. 19, 2011.

(30) Foreign Application Priority Data

Aug. 10, 2011  (FR) ...................... 11 57282

(51) Int. Cl.
  *A61B 17/16*   (2006.01)
  *A61F 2/46*    (2006.01)
  *A61F 2/30*    (2006.01)

(52) U.S. Cl.
  CPC ............. *A61B 17/16* (2013.01); *A61B 17/1637* (2013.01); *A61F 2/4603* (2013.01); *A61F 2/4607* (2013.01); *A61F 2/4612* (2013.01); *A61F 2002/30426* (2013.01); *A61F 2002/4619* (2013.01)

(58) Field of Classification Search
  CPC . F16B 21/04; A61F 2002/4619; A61B 17/92; A61B 17/16; A61B 17/1604; A61B 17/1659; A61B 17/1664; A61B 17/1666; A61B 17/1671; A61B 17/1684; A61B 17/14; A61B 17/1637

USPC ........ 606/79, 82–85, 86 R, 99, 100; 403/349; 408/204–206

See application file for complete search history.

(56) References Cited

U.S. PATENT DOCUMENTS

| | | | | |
|---|---|---|---|---|
| 448,126 | A * | 3/1891 | Craig | B32B 51/0473 408/204 |
| 1,065,456 | A * | 6/1913 | Lowrey | 294/50.6 |
| 1,123,730 | A * | 1/1915 | Greendfield | A61C 8/0039 433/165 |
| 2,444,099 | A * | 6/1948 | Hennessey, Jr. | 408/206 |
| 2,886,081 | A * | 5/1959 | Cowley | B21D 53/00 408/224 |
| 3,523,395 | A * | 8/1970 | Konrad | F16B 5/0233 29/433 |
| 3,609,056 | A * | 9/1971 | Hougen | 408/204 |
| 3,738,217 | A * | 6/1973 | Walker | 411/510 |
| 4,147,464 | A * | 4/1979 | Watson | B23B 51/05 408/206 |
| 4,250,600 | A * | 2/1981 | Gunther | F16B 21/04 411/350 |

(Continued)

OTHER PUBLICATIONS

French Search Report issued in Application No. FR1157282, dated Feb. 27, 2012, one page.

*Primary Examiner* — Matthew Lawson
*Assistant Examiner* — Amy Sipp
(74) *Attorney, Agent, or Firm* — Knobbe Martens Olson & Bear LLP

(57) ABSTRACT

A surgical tool, enabling extraction of a prosthesis from a bony implantation site of that prosthesis, defines a proximo-distal axis and includes a distal end head adapted both to cut at least partially the bonding interface between the prosthesis and the bony material of the implantation site and to fix itself to the prosthesis by rotation centered on the proximo-distal axis, according to embodiments of the present invention.

18 Claims, 4 Drawing Sheets

(56) References Cited

U.S. PATENT DOCUMENTS

| | | | |
|---|---|---|---|
| 4,623,353 A | 11/1986 | Buechel et al. | |
| 5,026,373 A * | 6/1991 | Ray | A61B 17/1637 606/279 |
| 5,044,393 A * | 9/1991 | Jiles | F16L 41/06 137/318 |
| 5,112,338 A * | 5/1992 | Anspach, III | A61F 2/4609 173/10 |
| 5,163,964 A | 11/1992 | Lazzeri et al. | |
| 5,171,277 A | 12/1992 | Roger | |
| 5,257,995 A | 11/1993 | Umber et al. | |
| 5,681,134 A * | 10/1997 | Ebert | 408/205 |
| 5,810,524 A * | 9/1998 | Wirth et al. | 408/203.5 |
| 5,820,315 A * | 10/1998 | Collard | 408/80 |
| 5,830,215 A * | 11/1998 | Incavo | A61B 17/1637 606/79 |
| 5,976,148 A * | 11/1999 | Charpenet et al. | 606/91 |
| 6,063,124 A * | 5/2000 | Amstutz | A61F 2/34 623/22.21 |
| 6,099,214 A * | 8/2000 | Lee | B23B 51/0406 408/204 |
| 6,132,469 A * | 10/2000 | Schroeder | A61F 2/4637 606/99 |
| 6,139,551 A * | 10/2000 | Michelson et al. | 606/79 |
| 6,174,335 B1 | 1/2001 | Varieur et al. | |
| 6,187,012 B1 | 2/2001 | Masini | |
| 6,264,657 B1 * | 7/2001 | Urbahns | A61B 17/1604 606/279 |
| 6,537,278 B1 * | 3/2003 | Johnson | 606/79 |
| 6,786,684 B1 * | 9/2004 | Ecker | B23B 51/0406 408/204 |
| 7,140,087 B1 * | 11/2006 | Giltner | 29/426.1 |
| 7,179,084 B1 * | 2/2007 | Kometas | A61C 8/0089 433/165 |
| 7,189,036 B1 * | 3/2007 | Watson | 408/204 |
| 7,476,228 B2 * | 1/2009 | Abdou | A61B 17/7059 606/104 |
| 7,637,703 B2 * | 12/2009 | Khangar et al. | 408/204 |
| 7,744,602 B2 * | 6/2010 | Teeny | A61F 2/4609 606/100 |
| 7,927,376 B2 * | 4/2011 | Leisinger | A61F 2/4637 606/91 |
| 8,221,037 B2 * | 7/2012 | Neitzell | 408/204 |
| 2002/0116007 A1 * | 8/2002 | Lewis | 606/99 |
| 2003/0031521 A1 * | 2/2003 | Haughton et al. | 408/203.5 |
| 2004/0186586 A1 * | 9/2004 | Seyer | A61F 2/4609 623/22.12 |
| 2004/0243136 A1 * | 12/2004 | Gupta | A61B 17/14 606/82 |
| 2005/0209597 A1 * | 9/2005 | Long | A61F 2/4607 606/86 R |
| 2006/0004378 A1 * | 1/2006 | Raines, Jr. | A61B 17/562 606/99 |
| 2006/0089656 A1 | 4/2006 | Allard et al. | |
| 2006/0195105 A1 * | 8/2006 | Teeny et al. | 606/76 |
| 2006/0200165 A1 * | 9/2006 | Tulkis | 606/99 |
| 2007/0010825 A1 * | 1/2007 | Leisinger | A61F 2/4637 606/99 |
| 2007/0123890 A1 * | 5/2007 | Way | A61B 17/320016 606/79 |
| 2007/0123893 A1 * | 5/2007 | O'Donoghue | A61B 17/14 606/82 |
| 2007/0123909 A1 * | 5/2007 | Rupp et al. | 606/104 |
| 2007/0212179 A1 * | 9/2007 | Khangar | B23B 51/0433 408/204 |
| 2007/0219562 A1 * | 9/2007 | Slone | A61F 2/34 606/99 |
| 2008/0077146 A1 * | 3/2008 | Pernsteiner | A61B 17/3213 606/79 |
| 2008/0195111 A1 * | 8/2008 | Anderson | 606/90 |
| 2010/0278601 A1 * | 11/2010 | Beynon | 408/1 R |
| 2011/0224673 A1 * | 9/2011 | Smith | A61F 2/4003 606/87 |
| 2014/0012272 A1 * | 1/2014 | Leisinger | A61F 2/4637 606/99 |

\* cited by examiner

OSTEOTOME EXTRACTOR

CROSS-REFERENCE TO RELATED APPLICATION

This application claims the benefit of U.S. Provisional Patent Application Ser. No. 61/509,506, filed on Jul. 19, 2011, and claims foreign priority to French Patent Application No. 20110057282, filed Aug. 10, 2011, both of which are incorporated by reference herein in their entireties for all purposes.

TECHNICAL FIELD

Embodiments of the present invention relate to a surgical tool for extraction of a prosthesis from a bony implantation site of that prosthesis as well as a surgical kit including such a surgical tool and such a prosthesis.

BACKGROUND

When a prosthesis has been implanted in a bone for a certain time, typically several years, it may prove necessary to remove the prosthesis for various reasons: for example, wear of the prosthesis, degeneration of the bony material of the prosthesis implantation site, trauma, and the like. The prosthesis removed is generally replaced by a revision prosthesis, the success and the implantation performance of which depend on the residual stock of bony material after removing the initial prosthesis. Consequently, surgeons aim to limit as much as possible any cutting of bony material necessary to free and extract the initial prosthesis.

With the arrival of prostheses with a porous surface or, more generally, adapted to have their surface colonized by the bone of the implantation site, extraction operations may prove particularly delicate. To this end, the surgeon generally employs osteotomes, the application of which may advantageously be guided to improve the precision of their action. Then, once the bonding interface between the prosthesis and the bony material has been cut in this way by these osteotomes, the surgeon uses another surgical tool to grasp and pull on the prosthesis in order to extract it.

SUMMARY

Embodiments of the present invention include an improved extraction surgical tool that facilitates and enhances the gestures of the surgeon. Embodiments of the present invention include a surgical tool for extraction of a prosthesis from a bony implantation site of that prosthesis, the surgical tool defining a proximo-distal axis and including a distal end head adapted both to cut at least partially the bonding interface between the prosthesis and the bony material of the implantation site and to fix itself to the prosthesis by a bayonet connection centered on the proximo-distal axis.

Embodiments of the present invention may also include a surgical kit, including a surgical tool as described above and a bone implantation prosthesis that includes a body to be anchored in the bony material of the implantation site, the anchor carrying externally at least part of the bonding interface between the prosthesis and the bony material of the implantation site and including a flange bearing on the implantation site, this flange being adapted to be fixed to the distal end head of the surgical tool by the bayonet connection.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
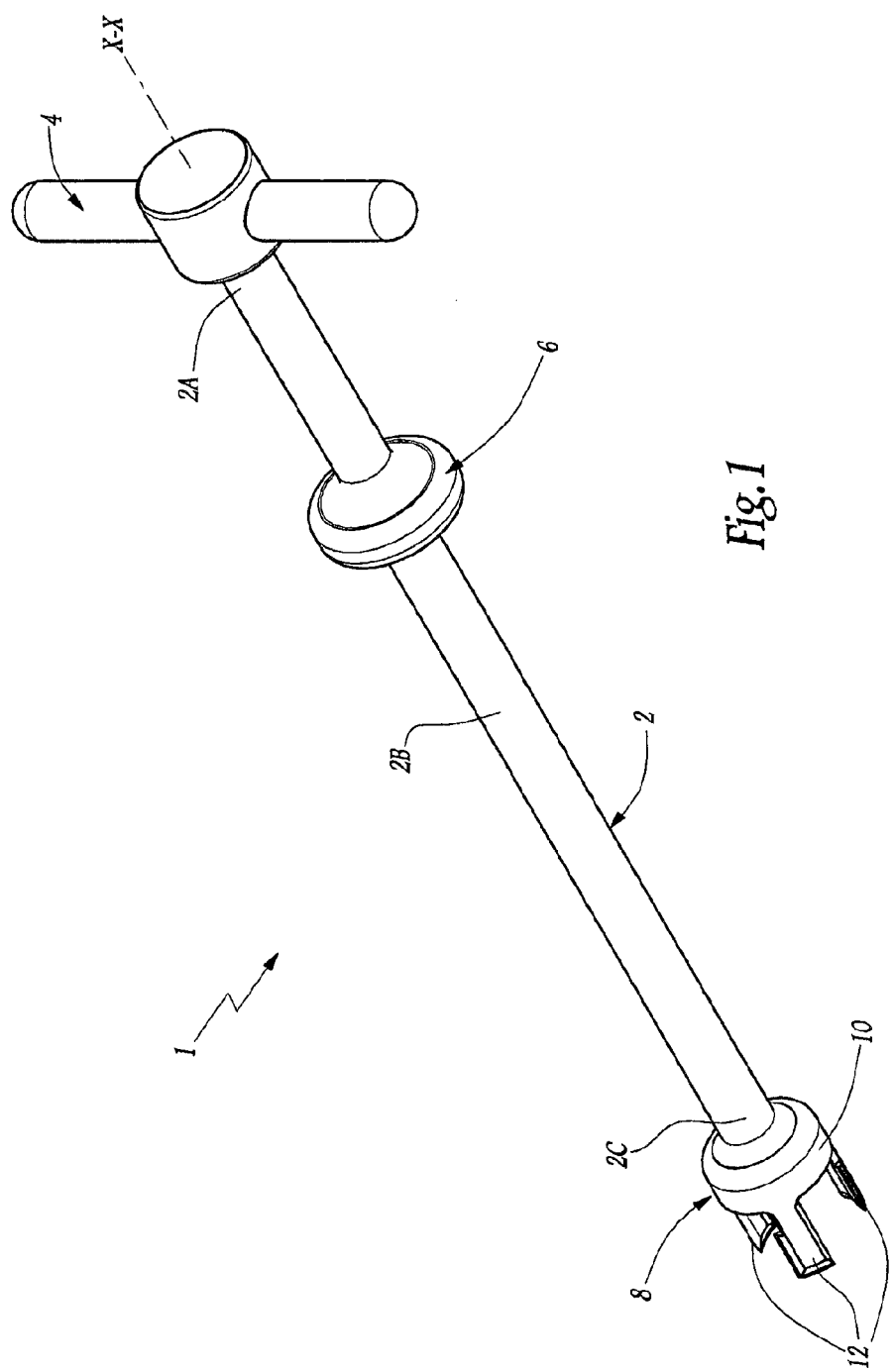
FIG. 1 is a perspective view of a surgical tool, according to embodiments of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 2:
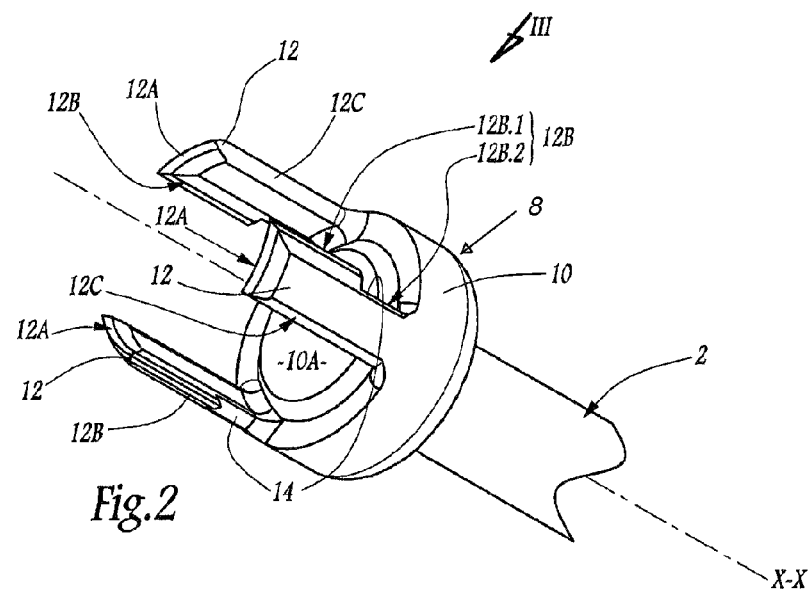
FIG. 2 is a perspective view as seen from a different angle and to a larger scale than FIG. 1 of a portion of the surgical tool from FIG. 1, according to embodiments of the present invention.
Figure 3:
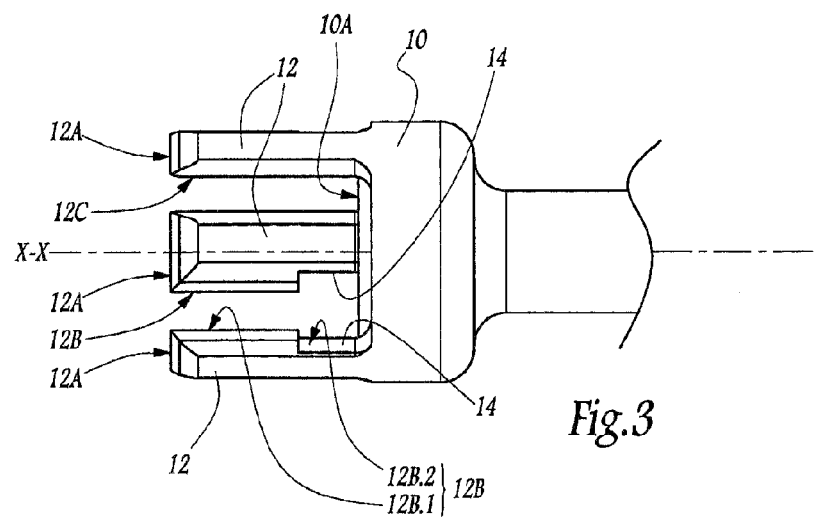
FIG. 3 is a view in elevation in the direction of the arrow III in FIG. 2, according to embodiments of the present invention.

In FIGS. 1 to 3 there is represented a surgical tool 1 for extracting a prosthesis from a bony implantation site of that prosthesis. As seen clearly in FIG. 1, this surgical tool 1 has an elongate overall shape, centered on a longitudinal axis X-X which, in use, extends in a direction which, at the proximal end, faces toward the surgeon and, at the distal end faces toward the bony implantation site of the prosthesis to be extracted.

The surgical tool 1 includes a shaft 2 that is centered on and extends lengthwise along the axis X-X and which includes a cylindrical rod of circular section. At its proximal end 2A, the shaft 2 is provided with a fixed handle 4 arranged transversely to the axis X-X, in order to facilitate driving, for example manual driving, of the surgical tool 1 by a user. This handle 4 may be formed in the shape of a "T". In its main part 2B, the shaft 2 is fixedly provided with a shoulder 6 projecting radially from the rest of the shaft 2. The shoulder 6 may be comprised of a disc centered on the axis X-X. Alternatively, shoulder 6 may be a cylindrical handle, a roughened surface, one or more indentations, one or more protrusions, or any other shape which permits shoulder 6 to receive a traction force and transmit the traction force to the shaft, according to embodiments of the present invention.

At its end 2C, the shaft 2 includes a fixed head 8 that cooperates mechanically with a prosthesis to be extracted. As illustrated in FIGS. 1 to 3, this head 8 includes a main body 10 that is centered on the axis X-X and is generally disc-shaped. According to one embodiment, the head 8 includes three elements 12, which may be separate and identical. In other embodiments, the head 8 may include one, two, three, four, five, six or more elements 12. In still other embodiments, the elements 12 may not be identical and one or more element 12 may have different lengths, widths, thicknesses, curvatures, or other features as compared to one or more other elements 12. Each element 12 may have a shape that is elongate in the direction of the axis X-X and projects in the longitudinal axial direction from the distal face 10A of the main body 10 of the head 8. According to some embodiments of the present invention, each element 12 projects from a portion of the external periphery of the distal face 10A of the body 10. Each element 12 as a whole corresponds to a portion of a tubular wall centered on the axis X-X and projecting axially from the exterior periphery of the face 10A of the body 10, according to embodiments of the present invention. Elements 12 may be referred to as cutting elements, according to embodiments of the present invention.

According to one embodiment, the three elements 12 are distributed, for example, in a substantially regular manner (e.g. separated by substantially the same radial angles) around the axis X-X. In particular, these three elements 12 may correspond to respective portions of the same tubular wall. According to other embodiments, the two or more elements 2 are distributed in an irregular manner on the distal head 8, and are either not separated by similar radial angles, and/or are not situated about a perimeter of the distal head 8. For example, the elements 12 may be positioned on distal head 8 at different or staggered radial distances from the axis X-X, and may be positioned at different or staggered radial separations with respect to the axis X-X.

As shown in FIGS. 1 to 3, each element 12 has, axially opposite its proximal end connecting the rest of the element to the main body 10 of the head 8, a distal free edge 12A along which a cutting edge is formed in a direction peripheral to the axis X-X. Each element 12 may be delimited in a direction peripheral to the axis X-X by two opposite longitudinal free edges 12B and 12C. The longitudinal edge 12B, which is that oriented in the clockwise direction about the axis X-X when the head 8 is viewed from the proximal end 2A of the shaft 2, has, in its longitudinal direction, a distal end part 12B.1 along which a cutting edge is formed and a proximal end part 12B.2 in which a recessed notch 14 is delimited. Edge 12B may also be referred to as leading edge 12B, and edge 12C may be referred to as trailing edge 12C, according to embodiments of the present invention.

An example of use of the surgical tool 1 will now be described with reference to FIGS. 4 to 6.

Figure 4:
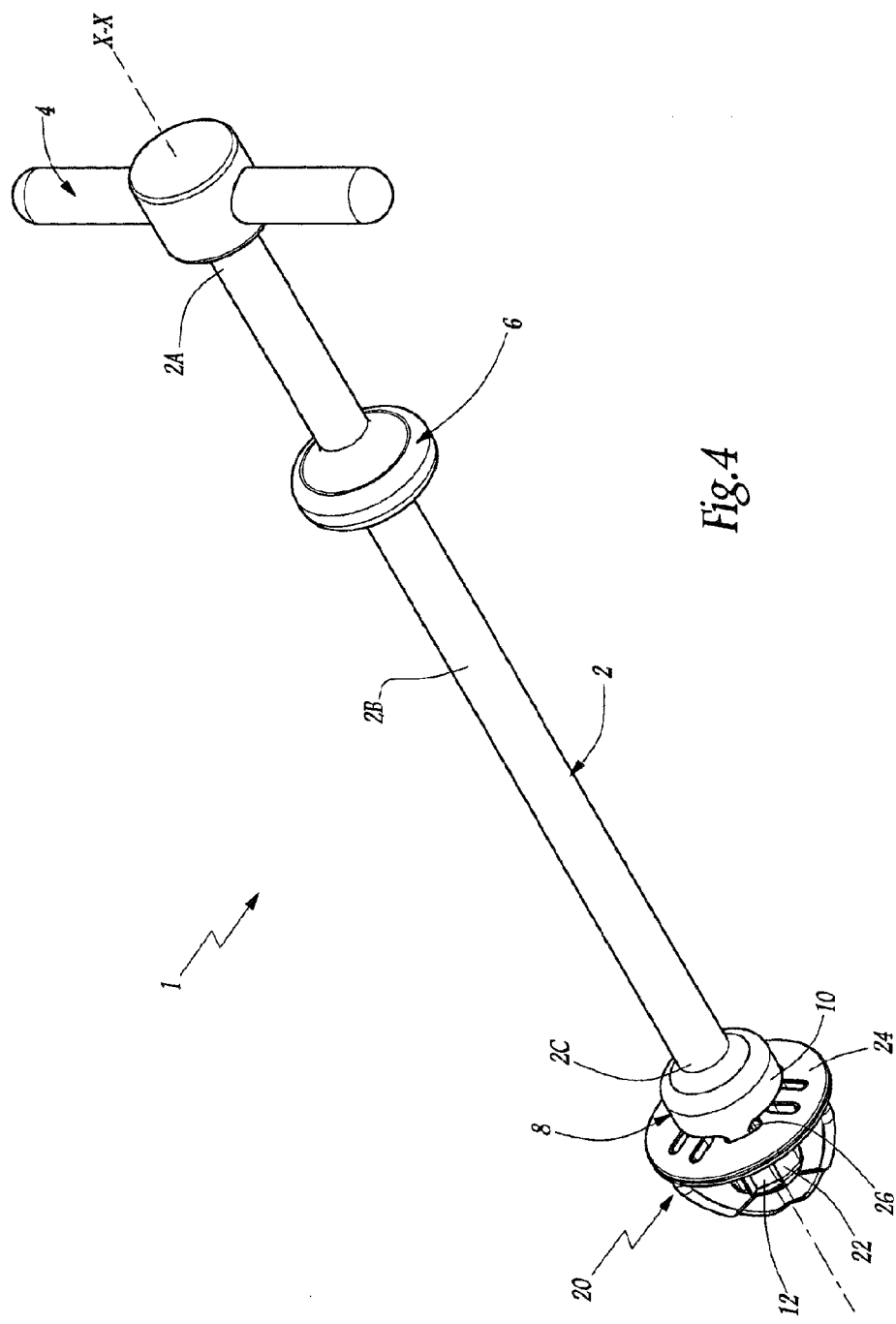
FIGS. 4 to 6 are views similar to FIGS. 1 to 3, respectively, showing the surgical tool from FIG. 1 associated with a prosthesis to be extracted with the aid of that surgical tool.
Figure 5:
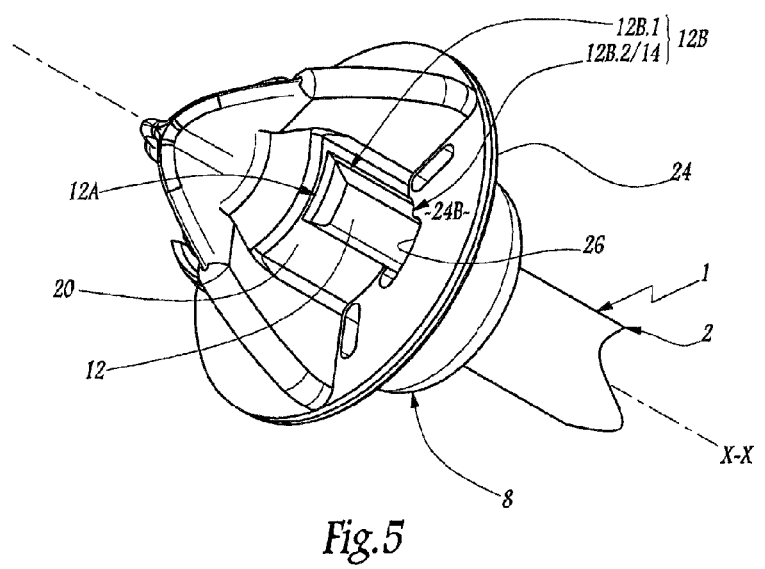
Figure 6:
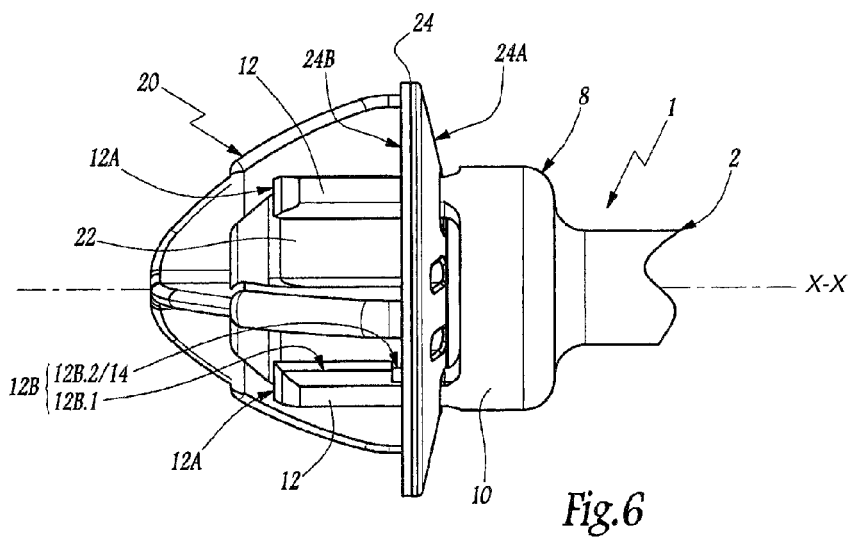

In these FIGS. 4 to 6, the head 8 of the surgical tool 1 cooperates with a prosthesis 20 to be extracted including an anchor body 22 anchored in the bony material of an implantation site of the prosthesis. This anchor body 22 is provided with a flange 24 which bears on the aforementioned implantation site. In some embodiments of the present invention, when the prosthesis 20 is in an implantation configuration, its body 22 is engaged depthwise in the bony material of the implantation site and its flange 24 remains outside or partially outside the bony material of the implantation site, bearing on the perimeter surface of the hole at the implantation site in which the body 22 is housed. Consequently, if a surgeon wishes to extract the prosthesis 20 from the aforementioned implantation site, the proximal face 24A of the flange 24 is directly accessible, whereas the distal face 24B of the flange 24 bears on the bony material of the implantation site. Given the context of the surgical intervention, the interface between the prosthesis 20, and more precisely the body 22 of that prosthesis, and the bony material of the implantation site proves resistant to extraction of the prosthesis 20 in the sense that, over time, a mechanical-biological bond has progressively formed at this interface between the prosthesis and the bony material. The strength of this bonding interface often proves particularly high in the situation in which the body 22 has a porous structure or, more generally, an exterior surface suitable for osteo-integration, as is generally the case when the prosthesis 20 is a prosthesis implanted without cement.

As used herein, the term "flange" is used in its broadest sense to refer to any structure or shape which has a proximal surface and a distal surface and is capable of contacting bone or being positioned on or near bone. For example, a flange may have a circular, square, rectangular, triangular, or other (regular or irregular) polygonal shaped cross-section along a dimension that is substantially perpendicular to the axis X-X, according to embodiments of the present invention. The perimeter of the flange may be smooth and/or continuously contoured, or may include straight segments, and/or may include a combination of both contoured and straight segments.

To extract the prosthesis 20, the surgeon grasps the shaft 2 of the surgical tool 1, notably by hand, and moves the head 8 toward the prosthesis 20, substantially aligning the axis X-X with a central geometrical axis of the prosthesis 20, in particular the central geometrical axis around which the flange 24 extends peripherally. The distal edge 12A of each element 12 of the head 8 can then be used to cut at least in part the bonding interface between the prosthesis 20 and the bony material of the implantation site. To this end, the flange 24 is provided with three through-slots 26 each of which connects the proximal face 24A and the distal face 24B of the flange 24 to each other. Each slot 26 has a cross section allowing, or even in some cases guiding, introduction into this slot of one of the elements 12, in a movement in translation oriented along the axis X-X and directed in the distal direction. In other words, each slot 26 may have a cross-sectional shape corresponding to a flat ring portion the width of which considered radially with respect to the axis X-X substantially corresponds to the radial thickness of each element 12 and the length of which, in a direction peripheral to the axis X-X, is substantially equal to the peripheral extent of the element 12, as illustrated in FIGS. 4 and 5, according to embodiments of the present invention.

The distal edge 12A of the elements 12 is introduced first into one of the slots 26 and projects therefrom, at the distal end, cutting the portion of the (bony) bonding interface between the prosthesis 20 and the bony material that it encounters on its trajectory in translation. The surgeon continues to drive the surgical tool 1 in translation distally along the axis X-X until the distal face 10A of the body 10 comes to bear against or in the immediate vicinity of the proximal face of the prosthesis 20, for example with the interior periphery of the proximal face 24A of the flange 24.

The surgeon then rotates the shaft 2 on itself about the axis X-X, in some cases using the handle 4 to increase the driving torque. In some cases, use of the handle 4 increases the driving torque tenfold. The head 8 is then driven in a similar rotary movement, causing the longitudinal edge 12B of each of its elements 12 to follow a circular trajectory, centered on the axis X-X, and, in the embodiment shown, in the clockwise direction. The distal end part 12B.1 of each of the edges 12B then cuts the part of the bonding interface between the body 22 of the prosthesis 20 and the bony material of the implantation site, situated on the circular trajectory of the edge 12B. At the same time, each notch 14 of the longitudinal edges 12 mechanically engages the flange 24 in the direction in which, given the rotary movement of the head 8 on itself about the axis X-X relative to the prosthesis 20, one of the peripheral ends of each slot 26 is introduced into the notch 14. This cases the slots 26 to become engaged, in a direction peripheral to the axis X-X, axially between the opposite axial edges of the notch 14. This rotation drive movement is continued by the surgeon so as to engage the flange 24 as far as to the bottom of the notches 14. The surgical tool 1 and the prosthesis 20 are then in the configuration of use represented in FIGS. 4 to 6.

Although notch 14 is shown as having an "L" shape, notch 14 may alternatively have other shapes, according to embodiments of the present invention. For example, the shape of notch 14 may be fully or partially curved, for example in a "U" shape, or may be segmented, for example in a "V" shape, according to embodiments of the present invention. Notch 14 may include any shape which is capable of accepting at least a portion of the inside edge of an aperture 26 upon rotation of the head 8, according to embodiments of the present invention. In one embodiment, the proximal end of notch 14 is delimited by a distal surface of the head 8 as shown in FIG. 3. In another embodiment, the proximal edge of notch 14 is located distally of the distal surface of the head 8. The shape of the proximal edge of the notch 14 may also take numerous forms, for example straight, curved, or a combination of straight and curved, according to embodiments of the present invention.

Although clockwise rotation is described, one of ordinary skill will appreciate, based on the present disclosure, that the tool 1 may alternatively be configured for counterclockwise rotation, according to embodiments of the present invention.

Upon engagement of the tool 1 with the prosthesis 20, the mechanical connection that the surgeon establishes between the head 8 of the surgical tool 1 and the flange 24 of the prosthesis 20 is a bayonet connection centered on the axis X-X, according to embodiments of the present invention.

The surgeon may exert a traction force along the axis X-X, directed in the proximal direction. The surgeon makes use of the shoulder 6, for example by mechanically engaging this shoulder 6 with an ad hoc tool (not shown), enabling the surgeon to increase (e.g. tenfold) the applied force to apply to the shaft 2 axial traction loads directed in the proximal direction. As the bonding interface between the prosthesis 20 and the bony material of the prosthesis implantation site has been cut in several areas, by the successive action of the distal edges 12A and the distal end parts 12B.1 of the longitudinal edges 12B of the elements 12, remaining uncut areas of this bonding interface are broken in a controlled manner as to their location, and easily, without the surgeon having to exert too great a traction force.

Thus the surgical tool 1 enables the prosthesis 20 to be extracted easily and quickly, it being noted that, due at least in part to its bayonet fixing, integrating partial cutting of the bonding interface between the prosthesis and the bony material of the implantation site, the surgeon does not need to use two separate instruments to turn and turn about to cut the aforementioned interface and then make the mechanical attachment to the prosthesis to be pulled.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. A system comprising:
   an implant comprising a plurality of apertures; and
   a tool for implant extraction, the tool comprising:
   a longitudinal axis and a distal head,
   wherein the distal head comprises a main body and a plurality of elongate cutting elements projecting from an external periphery of a distal face of the main body, the plurality of elongate cutting elements configured to at least partially cut an interface between the implant and bony material at an implantation site of the implant, each of the plurality of elongate cutting elements configured to extend through a corresponding one of said plurality of apertures of the implant and to couple with the corresponding one of said apertures upon rotation of the tool about the longitudinal axis; and
   wherein each of the plurality of cutting elements comprises a proximal portion and a distal end, the proximal portion having a reduced thickness in a circumferential direction compared to the distal end, the reduced thickness of the proximal portion being configured to facilitate coupling of the tool and the implant upon rotation of the tool about the longitudinal axis.

2. The system of claim 1, wherein the distal head is configured as a bayonet connection adapted to couple the distal head with the implant upon rotation of the distal head about the longitudinal axis.

3. The system of claim 1, wherein the plurality of cutting elements extend from the distal head substantially parallel to the longitudinal axis, wherein each of the plurality of cutting elements comprises:
   a distal edge configured to cut into bone; and
   a leading edge that is also configured to cut into bone, the leading edge including a notch configured to engage a slot edge of the implant.

4. The system of claim 3, wherein each of the plurality of cutting elements includes a proximal end adjacent to the distal head, and wherein the notch is located on the leading edge closer to the proximal end than to the distal edge.

5. The system of claim 4, wherein the notch is located on the leading edge at the proximal end.

6. The system of claim 3, wherein each of the plurality of cutting elements extends from the leading edge to a trailing edge along a portion of a virtual tubular wall centered on the longitudinal axis.

7. The system of claim 1, wherein the plurality of cutting elements are spaced apart by substantially the same circumferential separation.

8. The system of claim 7, wherein the plurality of cutting elements comprises at least three cutting elements.

9. The system of claim 1, wherein the tool further comprises a shaft extending along the longitudinal axis, wherein the distal end of the shaft is affixed to the distal head, and wherein a driving handle is affixed to a proximal end of the shaft.

10. The system of claim 9, wherein the shaft comprises a shoulder located between the driving handle and the distal head, and wherein the shoulder is configured to accept placement of a traction force on the shaft.

11. The system of claim 1, wherein the implant comprises a flange configured to bear on the implantation site, and wherein the flange is configured to couple with the tool upon rotation of the distal head about the longitudinal axis.

12. The system of claim 1, wherein the implant comprises a flange, the flange comprising a proximal surface and a distal surface, wherein the distal surface is configured to bear on the implantation site, wherein the flange comprises the plurality of apertures.

13. The system of claim 1, wherein each of the plurality of cutting elements comprises:
   a leading edge extending in a longitudinal direction; and
   a trailing edge opposite the leading edge and extending in the longitudinal direction.

14. The system of claim 1, wherein, in use, the distal end of each of the cutting elements is disposed at a distal-most edge of the cutting tool.

15. A system comprising:
   an implant comprising a plurality of apertures; and
   a tool for implant extraction, the tool comprising:

a longitudinal axis and a distal head,
wherein the distal head comprises a main body and a plurality of elongate cutting elements projecting longitudinally from a distal face of the main body, the plurality of elongate cutting elements being circumferentially spaced apart about a periphery of the distal face of the main body, the plurality of elongate cutting elements being configured to at least partially cut an interface between the implant and bony material at an implantation site of the implant;
wherein each of the plurality of cutting elements comprises:
    a leading edge extending in a longitudinal direction, the leading edge comprising a proximal portion and a distal portion, the distal portion comprising a cutting edge configured to cut into bone, the proximal portion comprising a notch; and
    a trailing edge opposite the leading edge and extending in a longitudinal direction;
    wherein the notch comprises a circumferential step projecting from the leading edge toward the trailing edge of at least one of the elongate cutting elements, and
    wherein, in use, the notch is configured to facilitate coupling of the tool and the implant upon rotation of the tool about the longitudinal axis.

16. The system of claim 15, wherein the cutting edge of each of the plurality of cutting elements extends from the notch to a distal edge of said cutting element.

17. The system of claim 15, wherein the cutting edge of each of the plurality of cutting elements is entirely radially inward of an outer periphery of the main body.

18. The system of claim 15, wherein there are no cutting edges disposed radially inwardly of the plurality of cutting elements disposed at the periphery of the distal face.

* * * * *